United States Patent [19]

Maurer et al.

[11] Patent Number: 5,597,812
[45] Date of Patent: Jan. 28, 1997

[54] PHOSPHORAMIDOTHIOATE AND PROCESS OF USE TO COMBAT PESTS

[75] Inventors: Fritz Maurer, Tochigi, Japan; Christoph Erdelen, Leichlingen, Germany; Ulrike Wachendorff-Neumann, Monheim, Germany; Jürgen Hartwig, Leichlingen, Germany; Andreas Turberg, Erkrath, Germany; Norbert Mencke, Leverkusen, Germany

[73] Assignee: Bayer Aktiengesellschaft, Leverkusen, Germany

[21] Appl. No.: 350,569

[22] Filed: Dec. 7, 1994

[30] Foreign Application Priority Data

Dec. 14, 1993 [DE] Germany ............... 43 42 621.2

[51] Int. Cl.$^6$ ............... A01N 57/30; C07F 9/24
[52] U.S. Cl. ............... 514/118; 558/171
[58] Field of Search ............... 558/171; 514/118

[56] References Cited

U.S. PATENT DOCUMENTS

| | | | |
|---|---|---|---|
| 4,870,065 | 9/1989 | Balogh et al. | 514/119 |
| 4,889,944 | 12/1989 | Balogh et al. | 558/171 |
| 4,980,346 | 12/1990 | Balogh et al. | 514/118 |
| 5,208,224 | 5/1993 | Bolton et al. | 514/118 X |

FOREIGN PATENT DOCUMENTS 216940  9/1944  United Kingdom .

OTHER PUBLICATIONS

Chemical Abstract vol. 93, Abstract No. 220697f p. 527 (1980).
Chemical Abstract vol. 66, Abstract No. 65818e p. 6218 (1967).
Chemical Abstract vol. 80, Abstract No. 47388z (1973).
Chemical Abstract vol. 114, Abstract No. 114:96830s pp. 251-252 (1991).
Chemical Abstract vol. 112, Abstract No. 112:93951e (1989).
English Abstract of HU 48-103, (1982).
Chemical Abstract vol. 115, Abstract No. 115:232364c (1991).

*Primary Examiner*—Jacqueline Haley
*Assistant Examiner*—Michael G. Ambrose
*Attorney, Agent, or Firm*—Sprung Horn Kramer & Woods

[57] ABSTRACT

The invention relates to phosphoric acid derivatives of the formula (I)

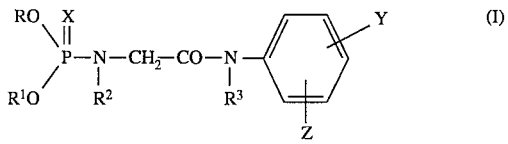

in which
R represents optionally substituted alkyl;
$R^1$ represents optionally substituted alkyl;
$R^2$ represents optionally substituted alkyl or optionally substituted alkenyl;
$R^3$ represents optionally substituted $C_4$–$C_6$-alkyl;
X represents oxygen or sulphur, and
Y and Z represent identical or different radicals from the series comprising hydrogen, halogen, alkyl and alkoxy, which can be used as pesticides.

3 Claims, No Drawings

PHOSPHORAMIDOTHIOATE AND PROCESS OF USE TO COMBAT PESTS

The invention relates to new phosphoric acid derivatives, to a process for their preparation, and to their use as pesticides, in particular as insecticides, acaricides and nematicides.

It has been disclosed that certain O,O-disubstituted thiophosphoryl-N,N-glycinamides have insecticidal, acaricidal and nematicidal properties (cf. U.S. Pat. No. 4,870,065). However, the activity of these known compounds is not always entirely satisfactory under certain circumstances, in particular when low concentrations and rates of active compound are applied.

The new phosphoric acid derivatives of the general formula (I)

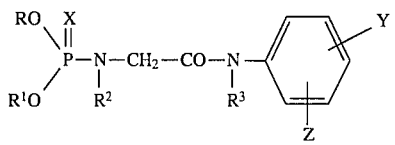

in which
R represents optionally substituted alkyl;
$R^1$ represents optionally substituted alkyl;
$R^2$ represents optionally substituted alkyl or optionally substituted alkenyl;
$R^3$ represents optionally substituted $C_4$–$C_6$-alkyl;
X represents oxygen or sulphur, and
Y and Z represent identical or different radicals from the series comprising hydrogen, halogen, alkyl and alkoxy
have now been found.

Furthermore, it has been found that the new phosphoric acid derivatives of the general formula (I) are obtained when
a) compounds of the general formula (II)

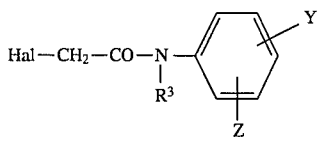

in which
$R^3$, Y and X have the abovementioned meanings and Hal represents halogen (preferably chlorine)
are reacted with compounds of the formula (III)

 (III)

in which
$R^2$ has the abovementioned meaning, and
b) the compounds of the general formula (IV)

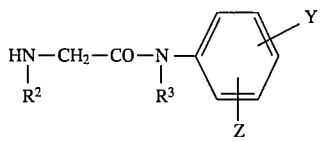

in which
$R^2$, $R^3$, Y and Z have the abovementioned meanings, which have been obtained in reaction step a), are reacted, if appropriate after their isolation, with compounds of the general formula (V)

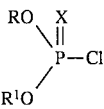

in which
R, $R^1$ and X have the abovementioned meanings,
if appropriate in the presence of an acid acceptor and if appropriate in the presence of a diluent.

The new compounds of the general formula (I) have properties which allow them to be used as pesticides. They display a powerful activity against arthropods and nematodes and can be used, in particular, for combating insects, mites and nematodes.

Preferred substituents, or ranges of the radicals listed in the formulae mentioned hereinabove and hereinbelow will be illustrated in the following text.

In the general formulae, alkyl as such or as component of a different radical, for example alkoxy, is to be understood as meaning straight-chain or branched alkyl having preferably 1 to 8 carbon atoms, in particular having 1 to 6 carbon atoms, particularly preferably having 1 to 5, and very particularly preferably 1 to 4, carbon atoms. The following may be mentioned as being preferred: methyl, ethyl, n- and i-propyl, n-, i-, s- and t-butyl, pentyl, hexyl and octyl. The alkyl radical $R^3$ is straightchain or branched (preferably branched) and contains preferably 4 or 5 (preferably 4) carbon atoms, with n-, i-, s- and t-butyl being mentioned as preferred and s- and i-butyl as particularly preferred.

In the general formulae, alkenyl denotes straight-chain or branched alkenyl having 2 to 6, in particular 2 to 4, carbon atoms, the allyl radical being mentioned as particularly preferred.

In the general formulae, halogen in Y and Z denotes fluorine, chlorine, bromine and/or iodine, preferably fluorine, chlorine and/or bromine, and particularly preferably fluorine and/or chlorine. Particularly preferably, one of the radicals Y and Z represents hydrogen, and very particularly preferably both Y and Z represent hydrogen.

The alkyl radicals R, $R^1$, $R^2$, and the alkenyl radical $R^2$ can be mono- or polysubstituted (preferably mono- to pentasubstituted, in particular mono- to trisubstituted) by identical or different substituents, preferred substituents which may be mentioned being halogen (preferably fluorine, chlorine, bromine and/or iodine, in particular fluorine and/or chlorine) and/or alkoxy having preferably 1 to 4, in particular 1 or 2, carbon atoms. The alkyl radicals R, $R^1$, $R^2$ and $R^3$ and the alkenyl radical $R^2$ are particularly preferably unsubstituted. In a further preferred embodiment, the alkyl radical $R^2$ carries an alkoxy radical having preferably 1 or 2 carbon atoms.

In the general formulae, X preferably represents sulphur.
In the general formulae,
R preferably represents $C_1$–$C_6$-alkyl which is optionally substituted by halogen (preferably fluorine and/or chlorine) and/or $C_1$–$C_4$-alkoxy.
In the general formulae,
$R^1$ preferably represents $C_1$–$C_6$-alkyl which is optionally substituted by halogen (preferably fluorine and/or chlorine) and/or $C_1$–$C_4$-alkoxy.
In the general formulae,
$R^2$ preferably represents $C_1$–$C_6$-alkyl or $C_2$–$C_6$-alkenyl, these radicals optionally being substituted by halogen (preferably fluorine and/or chlorine) and/or $C_1$–$C_4$-alkoxy.
In the general formulae,
$R^3$ preferably represents $C_4$–$C_6$-alkyl which is optionally substituted by halogen (preferably fluorine and/or chlorine) and/or $C_1$–$C_4$-alkoxy.

In the general formulae,

Y and Z preferably represent hydrogen, halogen (preferably fluorine and/or chlorine) and/or identical or different radicals from the series comprising $C_1$–$C_6$-alkyl and $C_1$–$C_6$-alkoxy.

In the general formulae,

R particularly preferably represents $C_1$–$C_4$-alkyl which is optionally substituted by halogen (preferably fluorine and/or chlorine) and/or $C_1$–$C_4$-alkoxy.

In the general formulae, $R^1$ particularly preferably represents $C_1$–$C_4$-alkyl which is optionally substituted by halogen (preferably fluorine and/or chlorine) and/or $C_1$–$C_4$-alkoxy.

In the general formulae, $R^2$ particularly preferably represents $C_1$–$C_4$-alkyl or $C_2$–$C_4$-alkenyl, these radicals optionally being substituted by halogen (preferably fluorine and/or chlorine) and/or $C_1$–$C_4$-alkoxy.

In the general formulae, $R^3$ particularly preferably represents $C_4$–$C_5$-alkyl which is optionally substituted by halogen (preferably fluorine and/or chlorine) and/or $C_1$–$C_4$-alkoxy.

In the general formulae,

Y and Z particularly preferably represent hydrogen, halogen (preferably fluorine and/or chlorine) and/or identical or different radicals from the series comprising $C_1$–$C_4$-alkyl and $C_1$–$C_4$-alkoxy.

In the general formulae,

R very particularly preferably represents $C_1$–$C_4$-alkyl which is optionally substituted by halogen (preferably fluorine and/or chlorine) and/or $C_1$–$C_2$-alkoxy.

In the general formulae, $R^1$ very particularly preferably represents $C_1$–$C_4$-alkyl which is optionally substituted by halogen (preferably fluorine and/or chlorine) and/or $C_1$–$C_2$-alkoxy.

In the general formulae, $R^2$ very particularly preferably represents $C_1$–$C_4$-alkyl or $C_2$–$C_4$-alkenyl, these radicals optionally being substituted by halogen (preferably fluorine and/or chlorine) and/or $C_1$–$C_2$-alkoxy.

In the general formulae, $R^3$ very particularly preferably represents $C_4$–$C_5$-alkyl which is optionally substituted by halogen (preferably fluorine and/or chlorine) and/or $C_1$–$C_2$-alkoxy.

In the general formulae,

Y and Z very particularly preferably represent hydrogen, halogen (preferably fluorine and/or chlorine) and/or identical or different radicals from the series comprising $C_1$–$C_2$-alkyl and $C_1$–$C_2$-alkoxy.

In the general formulae,

R especially represents $C_1$–$C_4$-alkyl.

In the general formulae,

R especially represents $C_1$–$C_4$-alkyl.

In the general formulae, $R^2$ especially represents $C_1$–$C_4$-alkyl, $C_1$–$C_2$-alkoxy-$C_1$–$C_4$-alkyl or allyl.

In the general formulae, $R^3$ especially represents $C_4$-alkyl.

In the general formulae,

Y and Z especially represent hydrogen or Y represents hydrogen and Z represents fluorine or chlorine.

In the general formulae,

R very especially represents methyl, ethyl or n-propyl, in particular ethyl.

In the general formulae, $R^1$ very especially represents methyl, ethyl, n-propyl and iso-propyl, in particular ethyl or i-propyl.

In the general formulae, $R^2$ very especially represents ethyl, i- and n-propyl, n-, i- and s-butyl, 2-methoxyethyl or allyl, in particular n-propyl.

In the general formulae, $R^3$ very especially represents n-, i-, s- or t-butyl, preferably n-, i- or s-butyl and in particular i- or s-butyl.

In the general formulae,

Y and Z very especially represent hydrogen.

In the general formulae,

X very especially represents sulphur.

The abovementioned definitions of radicals or illustrations which have been mentioned in general or in preferred ranges can be combined with each other, that is to say that any combinations between the particular ranges and preferred ranges are also possible. They apply to the end products and, analogously, to the precursors and the intermediates.

Preferred according to the invention are those compounds of the general formula (I) which contain a combination of the meanings mentioned above as being preferred.

Particularly preferred according to the invention are those compounds of the general formula (I) which contain a combination of the meanings mentioned above as being particularly preferred.

Very particularly preferred according to the invention are those compounds of the general formula (I) which contain a combination of the meanings which have been mentioned above as being very particularly preferred.

Special according to the invention are those compounds of the general formula (I) which contain a combination of the meanings mentioned above as being special.

Very special according to the invention are those compounds of the general formula (I) which contain a combination of the meanings mentioned above as very special.

If, for example, N-isobutyl-chloroacetanilide (2) and N-butylamine (3) are used as starting substances, the course of the reaction in process step a) according to the invention can be represented by the following equation:

$$\text{n-C}_4\text{H}_9\text{—NH}_2 + \text{Cl—CH}_2\text{—CO—N}\underset{\underset{\text{C}_4\text{H}_9\text{-i}}{|}}{\text{—}}\text{C}_6\text{H}_5 \longrightarrow$$
(3)           (2)

$$\text{n-C}_4\text{H}_9\text{—NH—CH}_2\text{—CO—N}\underset{\underset{\text{C}_4\text{H}_9\text{-i}}{|}}{\text{—}}\text{C}_6\text{H}_5$$
(4)

If, for example, the resulting N'-butylamino-N-n-isobutyl-acetanilide (4) and O,O-diethyl chlorothiophosphate (5) are used as starting substances, the course of the reaction in process step b) according to the invention can be represented by the following equation:

$$(4) + \begin{array}{c}\text{C}_2\text{H}_5\text{O}\\ \phantom{X}\searrow\\ \phantom{XX}\text{P—Cl}\\ \phantom{X}\nearrow\\ \text{C}_2\text{H}_5\text{O}\end{array}\overset{\text{S}}{\underset{\phantom{X}}{\|}} \xrightarrow[-\text{HCl}]{\text{base}}$$

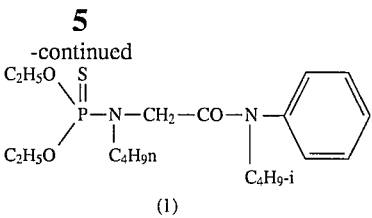

(1)

The starting substances of the general formulae II, III and V are known or can be obtained by known processes and methods.

The starting substances of the general formula (IV) are new. They and the process for their preparation in accordance with process step a) and their use as intermediates, preferably for the preparation of the compounds of the general formula (I), are part of the present invention.

Process steps a) and b) according to the invention for the preparation of the new compounds of the formula (I) are preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

Acid acceptors which can be employed in process step b) according to the invention are all acid-binding agents which can conventionally be used for such reactions. The following are preferably suitable: alkali metal hydrides and alkaline earth metal hydrides, such as lithium hydride, sodium hydride, potassium hydride and calcium hydride, alkali metal hydroxides and alkaline earth metal hydroxides, such as lithium hydroxide, sodium hydroxide, potassium hydroxide and calcium hydroxide, alkali metal carbonates, alkali metal hydrogen carbonates, alkaline earth metal carbonates and alkaline earth meal hydrogen carbonates, such as sodium carbonate, sodium hydrogen carbonate, potassium carbonate, potassium hydrogen carbonate and calcium carbonate, alkali metal acetates, such as sodium acetate and potassium acetate, alkali metal alcoholates, such as sodium tert-butylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethylaniline, pyridine, 2-methyl-, 3-methyl-, 4-methyl-, 2,4-dimethyl-, 2,6-dimethyl-, 2-ethyl-, 4-ethyl- and 5-ethyl-2-methylpyridine, 1,5-diazabicyclo-[4,3,0]-non-5-ene (DBN) , 1,8-diazabicyclo-[5,4,0]-undec-7-ene (DBU) and 1,4-diazabicyclo[2,2,2]-octane (DABCO).

The reaction temperatures in process steps a) and b) according to the invention can be varied within a substantial range. In general, the process steps are carried out at temperatures between 0° C. and 100° C., preferably at temperatures between 20° C. and 80° C.

In general, the process steps according to the invention are carried out under atmospheric pressure. However, they can also be carried out under elevated or reduced pressure.

To carry out the process steps according to the invention, the starting substances required in each case are preferably employed in approximately equimolar amounts. However, it is also possible to-use one of the components employed in each case in a larger excess. The reactions are carried out in a suitable diluent and, in the case of step b), in the presence of an acid acceptor, and the reaction mixture is stirred for several hours at the specific temperature required. Working-up in the process variants according to the invention is carried out in each case by customary methods (cf. the preparation examples).

The compounds of the general formula (IV) are preferably isolated in accordance with process step b) before they are reacted further.

In most cases, the new compounds of the formulae (I) and (IV) are obtained in the form of oils, some of which cannot be distilled without decomposition, but can be freed from the last volatile components by so-called "incipient distillation", i.e. by prolonged heating-under reduced pressure to moderately elevated temperatures, and purified in this manner. They can be characterized by way of example by the retention index or, in the case of the compounds of the formula (I), the shift in the $^{31}$P-NMR spectrum.

The active compounds of the formula (I) are suitable for combating animal pests, in particular insects, arachnids and nematodes, encountered in agriculture, in forestry, in the protection of stored products and of materials, and in the hygiene field, and have good plan tolerance and favorable toxicity to warm-blooded animals. They can preferably be used as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanita, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*

From the order of the Anoplura, for example, *Phylloxera vastatrix, Pemphigus spp., Pediculus humanus corporis, Haematopinus spp.* and *Linognathus spp.*

From the order of the Mallophaa, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp.,*

*Phorodon humuli, Rhoplosiphum padi, Empoasca spp., Euscelis bilobatus, Nephotettix cincticps, Lecanium corni, Saissetia oleae, naodelphax striatellus, Nilaparvata lugens, Aonidiella aurantii, Aspidiotus hederae, Pseudococcus spp.* and *Psylla spp.*

From the order of the Lepidoptera, for example, *Pect4inophora gossypiella, Bupalus piniarius, Cheimatobia brumata, nithocolletis blancardella, Hyponomeuta padella, Plutella maculipennis, Malacosoma neustria, Euproctis chrysorrhoea, nymantria spp., Bucculatrix thurberiella, Phyllocnistis citrella, Agrotis spp., Euxoa spp., Feltia spp., Earias insulana, Hellothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bissellleila, Tinea pellionella, Hofmnnophila pseudospretella, Cacoecia podana, Capua reticulana, Choristoneura fumiferana, Clysia ambiuella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomoriumpharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*

From the order of the Arachnida, for example, *Scorpio maurus* and *Latrodectus mactans.*

From the order of the Acarina, for example, *Acarus siro, Argas spp., Ornithodoros spp, Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp.*

The plant-parasitic nematodes include *Pratylnchus spp., Radopholus similis, Ditylenchus dipsaci, Tylenchulus semipenetrans, Heterodera spp., Meloidogyne spp., Aphelenchoides spp., Longidorus spp., Xiphinema spp.* and *Trichodorus spp.*

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and into formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents, liquefied gases under pressure, and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are also suitable for combating undesired pests, such as insects, ticks and mites in the sectors of animal keeping and cattle breeding; better results, for example higher milk production, greater weight, more attractive animal pelt, longer life etc., can be achieved by combating the pests.

The application of the active compounds according to the invention occurs in these sectors in a known fashion, such as by external application in the form of, for example, dipping, spraying, pouring-on and spotting-on.

The preparation of the compounds of the formula (I) according to the invention will be explained with reference to the examples below.

Unless otherwise indicated, percentages are by weight.

PREPARATION EXAMPLES

Example 1

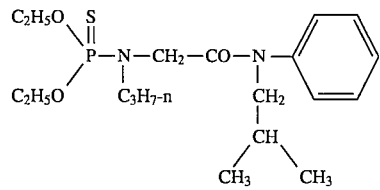

4.7 g (0.025 mol) of O,O-diethyl chlorothiophosphate are added at room temperature (approximately 20° C.) to a solution of 6.2 g (0.025 mol) of N-isobutyl-N'-n-propyl-aminoacetanilide and 3.8 g (0.0375 mol) of triethylamine in 50 ml of anhydrous methylene chloride, and stirring of the mixture is continued for 18 hours at room temperature (approximately 20° C.). The reaction mixture is then extracted twice using in each case 50 ml of water. The organic phase is dried over sodium sulphate and freed from solvent in vacuo. 9.1 g (91% of theory) of N-isobutyl-N'-n-propyl-N'-(O,O-diethyl-thiophosphoryl) aminoacetanilide remain in the form of an oil with a shift of 76.327 ppm in the $_{31}$P-NMR.

The following compounds of the formula (I)

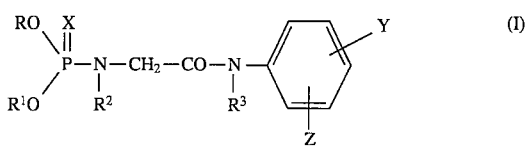

are obtained in accordance with Example 1.

TABLE 1

| Example No. | R | $R^1$ | $R^2$ | $R^3$ | X | Y | Z | $^{31}$P-NMR Shift (ppm) or refractive index $n_D^{20}$ |
|---|---|---|---|---|---|---|---|---|
| 2  | $C_2H_5$ | $i\text{-}C_3H_7$ | $i\text{-}C_4H_9$ | $i\text{-}C_4H_9$ | S | H | H | 74.913 |
| 3  | " | $C_2H_5$ | " | $n\text{-}C_4H_9$ | S | H | H | 76.358 |
| 4  | " | " | $C_2H_5$ | $i\text{-}C_4H_9$ | S | H | H | 76.284 |
| 5  | " | " | " | $n\text{-}C_4H_9$ | S | H | H | 75.873 |
| 6  | " | $i\text{-}C_3H_7$ | " | $i\text{-}C_4H_9$ | S | H | H | 74.943 |
| 7  | " | $C_2H_5$ | " | $sec\text{-}C_4H_9$ | S | H | H | 76.264 |
| 8  | " | $i\text{-}C_3H_7$ | " | " | S | H | H | 74.929 |
| 9  | " | $C_2H_5$ | $n\text{-}C_3H_7$ | " | S | H | H | 76.364 |
| 10 | " | $i\text{-}C_3H_7$ | " | " | S | H | H | 74.947 |
| 11 | " | $C_2H_5$ | $n\text{-}C_4H_9$ | $i\text{-}C_4H_7$ | S | H | H | 76.378 |
| 12 | " | $i\text{-}C_3H_7$ | " | " | S | H | H | 74.953 |
| 13 | " | $C_2H_5$ | $i\text{-}C_4H_9$ | " | S | H | H | 76.879 |
| 14 | " | $i\text{-}C_3H_7$ | " | " | S | H | H | 75.426 |
| 15 | " | $C_2H_5$ | $sec\text{-}C_4H_9$ | " | S | H | H | 75.895 |
| 16 | " | $i\text{-}C_3H_7$ | $i\text{-}C_3H_7$ | " | S | H | H | 74.569 |
| 17 | " | $C_2H_5$ | $CH_2CH_2OCH_3$ | " | S | H | H | 76.420 |
| 18 | " | $i\text{-}C_3H_7$ | " | " | S | H | H | 74.962 |

TABLE 1-continued

| Example No. | R | $R^1$ | $R^2$ | $R^3$ | X | Y | Z | $^{31}$P-NMR Shift (ppm) or refractive index $n_D^{20}$ |
|---|---|---|---|---|---|---|---|---|
| 19 | " | " | $n$-$C_3H_7$ | $n$-$C_4H_9$ | S | H | H | |
| 20 | " | $C_2H_5$ | " | $i$-$C_4H_9$ | S | H | H | |
| 21 | " | $i$-$C_3H_7$ | " | " | S | 4-F | H | $n_D^{20}$ |
| 22 | " | $C_2H_5$ | " | " | S | 3-Cl | H | 76.231 |
| 23 | " | $i$-$C_3H_7$ | " | " | S | 3-Cl | H | 74.828 |
| 24 | " | $C_2H_5$ | " | tert-$C_4H_9$ | S | H | H | 76.021 |
| 25 | " | $i$-$C_3H_7$ | " | " | S | H | H | 74.517 |
| 26 | " | $C_2H_5$ | $i$-$C_3H_7$ | $i$-$C_4H_9$ | S | H | H | |
| 26 | " | $i$-$C_3H_7$ | " | " | S | H | H | |
| 28 | $C_2H_5$ | $i$-$C_3H_7$ | $CH_2$—$CH$=$CH_2$ | $i$-$C_4H_9$ | S | H | H | 74.604 |
| 29 | " | $C_2H_5$ | " | " | S | H | H | 75.870 |
| 30 | " | $i$-$C_3H_7$ | $n$-$C_3H_7$ | $n$-$C_4H_9$ | S | H | H | |
| 31 | $C_2H_5$ | $C_2H_5$ | $n$-$C_3H_7$ | $i$-$C_4H_9$ | S | 3F | H | $n_D^{20} = 1.5064$ |
| 32 | $C_2H_5$ | $i$-$C_3H_7$ | $n$-$C_3H_7$ | $i$-$C_4H_9$ | S | 3F | H | $n_D^{20} = 1.5003$ |
| 33 | $C_2H_5$ | $C_2H_5$ | $n$-$C_3H_7$ | $i$-$C_4H_9$ | S | 3Cl | 4Cl | $n_D^{20} = 1.5274$ |
| 34 | $C_2H_5$ | $i$-$C_3H_7$ | $n$-$C_3H_7$ | $i$-$C_4H_9$ | S | 3Cl | 4Cl | $n_D^{20} = 1.5239$ |

The preparation of the novel N-alkyl-glycinanilides of the formula (IV), which are to be used as precursors, will be illustrated as follows:

Example a

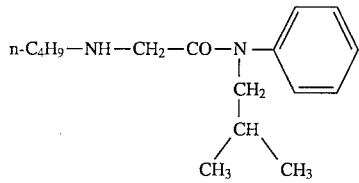

11.3 g (0.05 mol) of N-isobutyl-chloroacetanilide (preparation see Pestic. Chem., Proc. Int. Congr. Pestic. Chem., 2nd 1972, 5, 177–188; CA 80 (1974) 67293 t) are added to 30 ml of n-butylamine, and the mixture is allowed to stand for 18 hours at room temperature (approximately 20° C.). The excess butylamine is distilled off in vacuo, the residue is dissolved in 100 ml of methylene chloride, and the mixture is extracted twice using in each case 50 ml of water. The organic phase is dried over sodium sulphate and evaporated in vacuo. 10.5 g (80% of theory) of N-isobutyl-N'-n-butylaminoacetanilide are obtained as a colourless oil of retention index (OV) 1861.

The following compounds of the formula (IV)

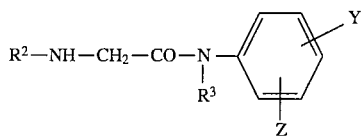

are obtained in accordance with Example a (Table 2):

TABLE 2

| Example | $R^2$ | $R^3$ | Y | Z | GC index (OV) or refractive index $n_D^{20}$ |
|---|---|---|---|---|---|
| b | $n$-$C_3H_9$ | sec-$C_4H_9$ | H | H | 1824 |
| c | $n$-$C_3H_7$ | $n$-$C_4H_9$ | H | H | 1872 |
| d | sec-$C_4H_9$ | iso-$C_4H_9$ | H | H | 1834 |
| e | $C_2H_5$ | $n$-$C_4H_9$ | H | H | 1758 |

TABLE 2-continued

| Example | $R^2$ | $R^3$ | Y | Z | GC index (OV) or refractive index $n_D^{20}$ |
|---|---|---|---|---|---|
| f | $C_2H_5$ | sec-$C_4H_9$ | H | H | 1745 |
| g | $n$-$C_3H_7$ | sec-$C_4H_9$ | H | H | 1832 |
| h | iso-$C_4H_9$ | iso-$C_4H_9$ | H | H | 1868 |
| i | sec-$C_4H_9$ | iso-$C_4H_9$ | H | H | 1852 |
| j | —$CH_2$—$CH_2$—$OCH_3$ | iso-$C_4H_9$ | H | H | 1845 |
| k | —$CH$—$CH$=$CH_2$ | iso-$C_4H_9$ | H | H | 1810 |
| l | $n$-$C_3H_7$ | $t$-$C_4H_9$ | H | H | 1749 |
| m | $n$-$C_3H_7$ | iso-$C_4H_9$ | 3-Cl | H | |
| n | $n$-$C_3H_7$ | iso-$C_4H_9$ | 4-F | H | |
| o | $n$-$C_3H_7$ | iso-$C_4H_9$ | 3F | H | $n_D^{20} = 1.5002$ |
| p | $n$-$C_3H_7$ | iso-$C_4H_9$ | 3Cl | 4Cl | $n_D^{20} = 1.5316$ |

The biological activity of the compounds of the formula (I) according to the invention will be illustrated with reference to the following examples:

Example A

Critical Concentration Test/Soil Insects

Test insect: *Diabrotica balteata* larvae in the soil

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration. The concentration of the active compound in the preparation is of practically no importance here, only the amount by weight of active compound per unit volume of soil, which is given in ppm (=mg/l), being decisive. The soil is transferred into 0.5 l pots and the pots are left to stand at 20° C.

Immediately after setting up the experiment, 5 pre-germinated maize kernels are introduced into each pot. After 1 day, the test insects are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the compounds of Preparation Examples 2, 6 and 8 showed a degree of effectiveness of 100% at an exemplary active compound concentration of 20 ppm.

Example B

Critical concentration Test/Nematodes

Test nematode: *Meloidogyne incognita*

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration.

The preparation of active compound is intimately mixed with the soil which is severely infested with the test nematodes. The concentration of the active compound in the preparation is of practically no importance here, only the amount by weight of active compound per unit volume of soil, which is given in ppm (=mg/l), being decisive. The treated soil is transferred into pots, lettuce is sown, and the pots are left to stand at a greenhouse temperature of 25° C.

After six weeks, the lettuce roots are examined for nematode invasion (root galls), and the degree of effectiveness of the active compound is determined in %. The degree of effectiveness is 100% if invasion is avoided completely and 0% if it is just as severe as in the case of the control plants in untreated, but equally infested, soil.

In this test, good activity was shown by the compounds according to the invention.

Example C

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration.

Cabbage leaves (*Brassica oleracea*) which are severely infested with the green peach aphid (*Myzus persicae*) are treated by being dipped into the preparation of active compound of the desired concentration.

After the specified periods of time, the destruction in % is determined. 100% means that all the aphids have been killed; 0% means that none of the aphids have been killed.

In this test, an effectiveness of 100% after 1 day was shown, for example, by the compound of Preparation Example 29 at an exemplary active compound concentration of 0.01%.

Example D

Nephotettix test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration.

Rice seedlings (*Oryza satira*) are treated by being dipped into the preparation of active compound of the desired concentration and are infested with larvae of the green rice leafhopper (*Nephotettix cincticeps*) while the seedlings are still moist.

After the specified periods of time, the destruction in % is determined. 100% means that all the leafhoppers have been killed; 0% means that none of the leafhoppers have been killed.

In this test, a degree of destruction of 100% after 6 days was shown, for example, by the compounds of Preparation Examples 4, 5, 6, 7, 9, 11, 14, 16, 17, 18, 28 and 29 at an exemplary active compound concentration of 0.02%.

Example E

Tetranychus test (OP resistant)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent, the stated amount of emulsifier is added, and the concentrate is diluted with water to the desired concentration.

Bean plants (*Phaseolus vulgaris*) which are severely infested with all development stages of the 2-spotted spider mite (*Tetranychus urticae*) are dipped into a preparation of active compound of the desired concentration.

After the specified periods of time, the destruction in % is determined. 100% means that all the spider mites have been killed; 0% means that none of the spider mites have been killed.

In this test, an effectiveness of 100% after 7 days was shown, for example, by the compounds of Preparation Examples 2, 4, 6, 7, 8, 9, 13, 14, 18, 26, 28 and 29 at an exemplary active compound concentration of 0.01%.

Example F

Fly test (*Musca domestica*)

Test insects: Adult *Musca domestica*, strain WHO (N)

Emulsifier: 35 parts by weight of ethylene glycol monomethyl ether 35 parts by weight of nonylphenyl poly glycol ether To produce a suitable formulation, three parts by weight of active compound are mixed with seven parts of the abovementioned solvent/emulsifier mixture, and the resulting emulsion concentrate is diluted with water to the desired concentration in each case.

2 ml of this preparation of active compound are pipetted onto filter paper discs (⊖9.5 cm) which are located in Petri dishes of a corresponding size. After the filter paper discs have dried, 25 test insects are introduced into the Petri dishes, and the dishes are covered.

After 1, 3, 5 and 24 hours, the effectiveness of the preparation of active compound is determined. 100% means that all the flies have been killed; 0% means that none of the flies have been killed.

In this test, an effectiveness of 100% was shown, for example, by the compound of Preparation Example 11 at an exemplary concentration of active compound of 1000 ppm.

Example G

Test with *Boophilus microplus* resistant/SP-resistant Parkhurst strain

Test insects: Adult females which have sucked themselves full

Solvent:
  35 parts by weight of ethylene glycol monomethyl ether
  35 parts by weight of nonylphenyl polyglycol ether To produce a suitable formulation, three parts by weight of active compound are mixed with seven parts of the abovementioned solvent/emulsifier mixture, and the resulting emulsion concentrate is diluted with water to the desired concentration in each case.

10 resistant adult *Boophilus microplus* specimens are immersed for 1 minute into the test preparation of active compound. After they have been transferred to plastic beakers and stored in a controlled-environment cabinet, the degree of destruction is determined.

100% means that all the ticks have been killed; 0% means that none of the ticks have been killed.

In this test, an effectiveness of 100% was shown, for example, by the compounds of Preparation Examples 9 and 10 at an exemplary active compound concentration of 1000 ppm.

We claim:

1. A compound of the formula

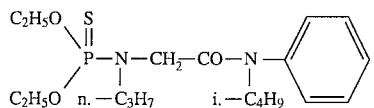

2. A pesticidal composition, which comprises as an active ingredient a pesticidally effective amount of the phosphoric acid derivative according to claim 1 and a diluent.

3. A method for combating pests which comprises applying to such pest or to a pest habitat a pesticidally effective amount of the phosphoric acid derivative according to claim 1.

* * * * *